United States Patent [19]
Franzmair

[11] 3,988,345
[45] Oct. 26, 1976

[54] IMIDAZOLINE DERIVATIVES AND THE PREPARATION THEREOF

[75] Inventor: Rudolf Franzmair, Linz-Ebelsberg, Austria

[73] Assignee: Chemie Linz Aktiengesellschaft, Austria

[22] Filed: Apr. 7, 1975

[21] Appl. No.: 565,762

[30] Foreign Application Priority Data
Apr. 5, 1974  Austria ............................... 2854/74

[52] U.S. Cl. ........................ 260/309.6; 260/309.7; 424/273
[51] Int. Cl.² ......................................... C07D 49/34
[58] Field of Search ...................... 260/309.6, 309.7

[56] References Cited
UNITED STATES PATENTS
3,931,216  1/1976  Franzmair ....................... 260/309.6

FOREIGN PATENTS OR APPLICATIONS
741,947  5/1970  Belgium ............................ 260/309.6
632,578  11/1963  Belgium ............................ 260/309.7

OTHER PUBLICATIONS
Najer et al., Bull'n Soc. Chim. France, 1961, pp. 2114–2126.

Primary Examiner—Ethel G. Love
Attorney, Agent, or Firm—Wenderoth, Lind & Ponack

[57] ABSTRACT

A process for the preparation of 2-(substituted aryl)amino-2-imidazoline derivatives by reacting appropriate substituted aniline derivatives with 1-aroyl-imidazoline-2-ones in the presence of at least two mols of phosphorus oxychloride per mol of the aniline derivative and optionally hydrolyzing the resulting intermediate compound. Certain novel 2-dihaloarylamino-2-imidazoline derivatives with hypotensive action are also disclosed.

14 Claims, No Drawings

IMIDAZOLINE DERIVATIVES AND THE PREPARATION THEREOF

This invention relates to a process for the preparation of imidazoline derivatives, more particularly 2-arylamino-2-imidazoline derivatives, and also to certain novel 2-dihaloarylamino-2-imidazoline derivatives. The invention is also concerned with pharmaceutical compositions containing the said imidazoline derivatives.

It is known from Austrian Patent Specification No. 248,428, No. 250,344 and No. 250,345 that 2-arylamino-2-imidazoline derivatives, especially the compound 2-(2',6'-dichlorophenylamino)-2-imidazoline possess a pronounced hypotensive action coupled with a sedative action.

It is further disclosed in Belgian Patent Specification No. 741,947 that N-aroyl derivatives of these 2-arylamino-2-imidazoline derivatives, for example 2-[N-benzoyl-(2',6'-dichlorophenyl)-amino] -2-imidazoline, also exhibit this hypotensive and at the same time sedative action.

The processes hitherto used for the preparation of these 2-arylamino-2-imidazoline derivatives, above all of 2-(2',6'-dichlorophenylamino)-2-imidazoline, are based on the condensation of ethylenediamine with derivatives of appropriately substituted anilines in which the amino group beforehand has been converted into a thiourea, isothiuronium, guanidine or isocyanide-dihalide group. (See Austrian Patent Specifications No. 248,428, No. 250,344 and No. 250,345, or No. 278,000, No. 278,776 and No. 284,838).

However, these processes all suffer from the disadvantage that only relatively low yields are achievable and in addition, in many of these processes, an unpleasant evolution of gases containing sulphur such as, for example, $H_2S$, has to be tolerated.

2-Arylamino-2-imidazoline derivatives which contain a halogen atom, a trifluoromethyl group or a cyano group on the aromatic nucleus and which in addition carry a methyl or methoxy group but not 2,6-dichloroaryl-2-imidazolines, also may be manufactured by reaction of the appropriately substituted anilines with alkylmercaptoimadazoline or bis-(2-oxo-1-imidazolidinyl)-phosphine chloride (see Austrian Patent Specification No. 266,826). The yield from this process is not quoted. In the reaction with alkylmercaptoimidazoline, the elimination of mercaptan which occurs during the reaction is also a disadvantage.

According to Belgian Patent Specification No. 741,947, the N-aroyl derivatives of the 2-arylamino-2-imidazoline derivatives are only obtainable via aroylation of the free 2-arylamino-2-imidazolines with the corresponding acid chlorides.

It has now been found that 2-arylamino-2-imidazolines may be prepared more simply and more economically, and in incomparably better yields, by reaction of the appropriately substituted anilines with 1-aroylimidazolidin-2-ones followed by neutralisation or saponification of the resulting intermediate products, if the reaction is carried out in the presence of phosphorus oxychloride. The intermediate products obtained after neutralisation of the acid reaction mixture are aroyl derivatives of these 2-arylamino-2-imidazolines, which are not the same as the aroyl derivatives described in Belgian Patent Specification No. 741,947, as is demonstrable, inter alia, by the mixed melting point, and instead carry the aroyl group on an imidazoline nitrogen atom. In these aroyl derivatives, which are obtained in a pure form, the aroyl group very easily may be split off by saponification, whereby the 2-arylamino-2-imidazolines are obtained in a particularly pure form.

In accordance with the present invention there is provided a process for the preparation of a 2-arylamino-2-imidazoline derivative having the general formula

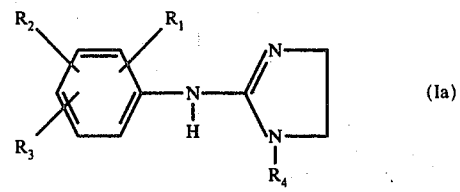

(Ia)

or

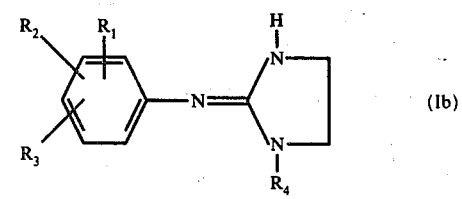

(Ib)

in which each of $R_1$, $R_2$ and $R_3$, which may be the same or different, is a hydrogen atom or a halogen atom, preferably chlorine or bromine, a lower alkyl group, a lower alkoxy group or a nitro group, with the proviso that at least one of $R_1$, $R_2$ and $R_3$ is not a hydrogen atom, and $R_4$ is a hydrogen atom or $R_5$, wherein $R_5$ is a benzoyl group which, optionally may be substituted by a methyl or ethyl group, or a salt thereof, which comprises reacting an aniline derivative having the general formula:

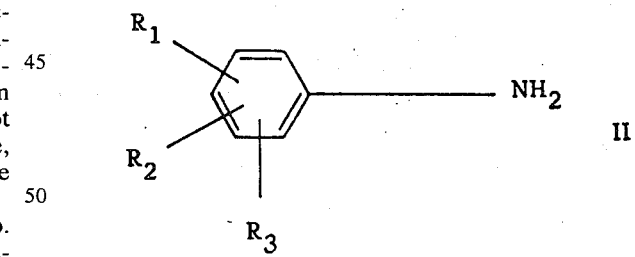

II in which $R_1$, $R_2$ and $R_3$ are as defined above, with a 1-aroyl-imidazolidin-2-one having the general formula

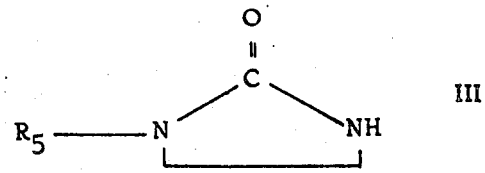

III in which $R_5$ is as defined above, in the presence of at least 2 mols of phosphorus oxychloride per mol of the aniline derivative of the formula II at a temperature from room temperature to the boiling point of phosphorus oxychloride, and subjecting the intermediate compound obtained after removing excess phosphorus oxychloride to mild hydrolysis, after which, if desired, in the resulting compound of formula I in which $R_4$ is $R_5$, the aroyl group is split off by treatment with an alcohol, acid or alkaline compound and the resulting compound of formula Ia or Ib is isolated as the free base or a salt with an inorganic or organic acid.

As a rule, the aniline derivative of the formula II and the 1-aroylimidazolidin-2-one of the formula III are preferably employed in approximately equimolar amounts. It is also possible to use either of the reactants in slight excess, for example an excess of 10 to 20% by weight relative to the amount of the other reactant. Even if a substantially greater excess is used, the reaction in principle takes place in the same sense, but certain losses in yield, for example a reduction in yield to 75%, must be expected because of side reactions which take place.

Suitably, at least 3 mols of phosphorus oxychloride are employed per mol of aniline derivative of the formula II, because this gives optimum purity of the end product of the formula I. The simultaneous use of phosphorus oxychloride as the solvent for the reactants is particularly preferred. However, the reaction also may be carried out in an inert organic solvent, for example in a chlorohydrocarbon, as the reaction medium.

After completion of the reaction, it is expedient to remove the excess phosphorus oxychloride, which is preferably done by distillation. The acid evaporation residue then contains an intermediate product, containing phosphorus, which in most cases crystallises and on treatment with cold water, for example ice water, and even more rapidly on treatment with an aqueous alkaline medium, such as, for example, sodium carbonate solution or dilute sodium hydroxide solution, is hydrolysed to a compound of the formula I in which $R_4$ is $R_5$. This mild hydrolysis may be effected either by direct addition of the aqueous medium to the evaporation residue or by dissolving the residue in an organic solvent such as, for example, methylene chloride, and treating the solvent with optionally ice-cooled water or an alkaline solution.

The splitting off of the aroyl group, for the purpose of preparing a compound of the formula I, may be carried out either with an acid, namely a mineral acid such as for example hydrochloric acid, hydrobromic acid, sulfuric acid, phosphoric acid and perchloric acid or an organic acid which may be a monocarboxylic acid such as acetic acid, propionic acid, benzoic acid or a polycarboxylic acid such as oxalic acid, citric acid, or tartaric acid, or with an alkaline reagent, such as a solution of sodium hydroxide, potassium hydroxide, sodium or potassium carbonate or other salts of sodium or potassium, which as solution in water give an alkaline reaction. Furthermore ammonia, a primary, secondary or tertiary alkylamine, for example n-butylamine, arylamines such as aniline, alkanolamines such as ethanolamine, aralkylamines such as benzylamine and cyclic imines such as piperidine; or an alkali metal alcoholate can be used as splitting agent.

In some cases, the treatment with the reagent to be used for the splitting reaction may be carried out without using an added solvent, for example when splitting with a dilute acid or caustic alkali or with an organic amine. Where the splitting reagent is a solid or the compound of the formula I in which $R_4$ is $R_5$ is insufficiently soluble, it is advisable to add a suitable solvent or diluent. In most cases it is advisable to carry out the saponification at an elevated temperature, for example at a temperature between 60° and 120° C, expediently at the boiling point of the reaction medium, in order to avoid excessively long reaction times. The duration of heating is in that case mostly in excess of one hour and expediently several hours.

Surprisingly, it has been found that the aroyl group may be split off with a lower aliphatic alcohol, and, in particular, preferably with a primary alcohol, and that this takes place particularly advantageously. As a rule, it is advisable to dissolve the aroyl compound in the alcohol and to boil the solution under reflux. The splitting reaction is very gentle if this procedure is followed, the yield is more than 90% and practically no by-products are formed.

If it is desired to prepare a compound of the formula I in which $R_4$ is a hydrogen atom, it is also possible to carry out the splitting of the intermediate compound containing phosphorus, and the saponification of the aroyl compound of the formula I resulting therefrom, in one process step. In this case, the excess phosphorus oxychloride is removed from the condensation reaction product by distillation, after which the splitting reagent, for example an alcohol, is added directly and the mixture is heated. The end product obtained after the splitting and saponification have been carried out is nevertheless obtained completely pure and the total yield, relative to the aniline derivative of the formula II, may be increased further by following this method.

This one-step reaction has proved of value especially for the preparation of the known active compound 2-(2',6'-dichlorophenylamino)-2-imidazoline, which has become particularly advantageously accessible by this new process.

The compound of the formula I wherein $R_4$ is a hydrogen atom may be isolated either directly as the base or, after acidification, in the form of a salt. If, for example, the aroyl group is split off with an acid, the salt, for example the hydrochloride, in many cases precipitates from the aqueous solution as crystals and may be obtained directly in the pure state by filtering it off.

The compound of the formula I in which $R_4$ is $R_5$, which is obtained in a solid form on mild hydrolysis, is a homogeneous, well-crystallised compound in which the structure is difficult to determine unambiguously. On the basis of the IR spectrum and NMR spectrum it may be assumed that the aroyl group is bonded to one of the two nitrogen atoms in the imidazoline ring and not to the aniline nitrogen, in contrast to the aroyl compounds which are described in Belgian Patent Specification No. 741,947, and which carry the aroyl group on the aniline nitrogen atom.

At the same time the possibility that the compounds may have an exocyclic double bond, cannot be excluded entirely.

This compounds of formula Ia and b, in which $R_4$ is $R_5$ are valuable intermediate products in the preparation of the known valuable compounds of formula Ia and b, in which $R_4$ is hydrogen.

The present invention also provides a compound having the general formula:

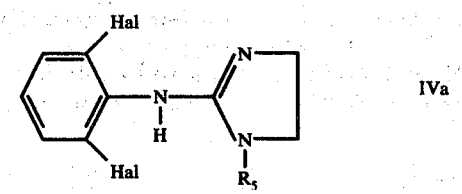

IVa or

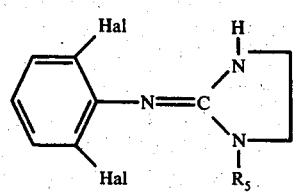

IVb in which Hal is a chlorine or bromine atom and $R_5$ is as defined in formula I.

In the preparation of a compound of formula IVa or IVb according to the process described above a 2,6-dihaloaniline is used as the starting material.

It has been found that compounds of formulae IVa and IVb have very interesting pharmaceutical properties. Thus, for example, compounds of the formulae IVa and IVb, in which $R_5$ is a benzoyl or o-, m- or p-toluyl group, also have a hypotensive action, like the known compounds of formula I in which $R_4$ is a hydrogen atom and like the aroyl derivatives of these compounds, described in Belgian Patent Specification No. 741,947, which are substituted at the aniline nitrogen atom, but the sedative component of their action is substantially less pronounced. A particularly advantageous relation of hypotensive action to sedative action is to be found in the case of the compound in which $R_5$ is a benzoyl group, so that when this compound is used as a hypotensive agent, the fatigue, which inter alia, manifests itself as an unpleasant side effect, does not occur. All these compounds show excellent oral resorption, particularly the compound where $R_5$ is a benzoyl group.

The same type of action is also to be observed with other compounds of the formula IVa or IVb, though to a different degree.

The absence of the sedative or central-depressant action easily may be established by ascertaining the presence of the carotid sinus reflex on narcotised rabbits after administration of the abovementioned compounds of the formula IVa or IVb in doses of 100 micrograms/kg. This reflex is almost completely suppressed on administration of the same dose of 2-(2',6'-dichlorophenylamino)-2-imidazoline.

It is further demonstrated by the unchanged behavior of awake mice after administration of 5 or 10 mg/kg of the benzoyl compound of the formula IVa or IVb.

The compounds of the formula IVa or IVb, especially those in which $R_5$ is a benzoyl group, therefore, may be used in medicine as hypotensive agents, in all forms of preparation customary for pharmaceutical purposes, such as tablets, dragees, capsules, suppositories, emulsions, solutions or injection solutions.

Accordingly the present invention further provides a pharmaceutical composition comprising, as the active ingredient, a compound of formula IVa or IVb, in admixture with a pharmacologically-acceptable diluent or carrier.

Depending on the form used for administration, either the free base or a salt may be employed. Salts used are, for example, those with inorganic or organic acids, such as hydrohalides, phosphates, oxalates, 8-chlorotheophyllinates or salts with acid synthetic resins.

The 1-aroylimidazolidin-2-ones of the formula III used as the starting material are new, with a few exceptions. They may be obtained by aroylation of ethyleneurea.

The Examples which follow illustrate the invention and the manner in which it may be performed.

The NMR absorptions indicated in these Examples are quoted in δ-values.

EXAMPLE 1

16.2 g. of 2,6-dichloroaniline and 20.92 g. of 1-benzoylimidazolidin-2-one (10% excess) in 146 ml of phosphorus oxychloride ($POCl_3$) are stirred for 70 hours at 50° C. The excess $POCl_3$ is distilled off in vacuo, ice water is added to the crystals which remain and the mixture is shaken for ½ hour at 0° C. It is then rendered alkaline with 40% strength aqueous sodium hydroxide solution whilst cooling with ice and the aqueous phase is extracted three times with chloroform. The combined chloroform phases are shaken once thoroughly with 1 N sodium hydroxide solution, washed with water until neutral, dried over sodium sulphate and evaporated to dryness in vacuo. The colorless residue is triturated hot with cyclohexane, cooled to room temperature, filtered off, washed and dried.

Yield of 1-benzoyl-2-(2', 6'-dichlorophenylamino)-2-imidazoline: 30.0 g. representing 89.8% of theory. For analysis, the product is recrystallised from isopropanol.

Melting point: 160° to 162° C

Analysis: $C_{16}H_{13}Cl_2N_3O$: Calculated: C,57.19; H,3.98; N,12.55; O,5.23; Cl,21.10. Found: C,57.4; H,4.1; N,12.4; O,5.2; Cl,20.8.

pKa: 4.01 (in 70% strength methylCellosolve at room temperature)

UV: $\lambda$ = 237 nm (sh; $\epsilon$. = 22,100) in ethanol.

IR: (KBr) 3,310 $cm^{-1}$, 1,686 $cm^{-1}$, 1,656 $cm^{-1}$, 1,612 $cm^{-1}$ and 1,579 $cm^{-1}$.

NMR: (100 MHz, $CDCl_3$): 3.42 (2H, approximate triplet), 4.01 (2H, approximate triplet), approx. 4.10 (m, broad, NH, exchanges with $D_2O$).

2-[N-Benzoyl-(2',6'-dichlorophenyl)-amino]-2-imidazoline according to Belgian Patent Specification No. 741,947 also has a melting point of 160° to 161° C but the two compounds have a mixed melting point of 134° to 143° C.

The other characteristic data of the compound according to the Belgian Patent Specification are:

PKa value = 6.10 (in 70% strength methylCellosolve at room temperature)

NMR: (100 MHz, $CDCl_3$): 3.66 (s, 4H), 6.43 (m, broad, NH, exchanges with $D_2O$); thus these data are also markedly different.

EXAMPLE 2

12.0 g. of 1-benzoyl-2-(2',6'-dichlorophenylamino)-2-imidazoline, prepared according to Example 1, are boiled in 150 ml. of methanol for 6 hours under reflux. The mixture is completely concentrated by evaporation in vacuo, the yellowish resinous residue is dissolved in 30 ml. of hot ethanol, the solution is cooled to 0° C and mixed with 10 ml. of 20% strength hydrochloric acid in ethanol, 60 ml. of ether are added and the whole is left to stand for 20 minutes at 0° C. The crystals are filtered off, washed with ether and dried. Yield: 9.20 g of 2-(2',6'-dichlorophenylamino)-2-imidazoline, representing 96.3% of theory.

The substance is obtained in an analytically pure form.

EXAMPLE 3

8.1 g. of 2,6-dichloroaniline and 10.45 g. of 1-benzoyl-2-imidazolidin-2-one are stirred with 73 ml. of POCl$_3$ for 70 hours at 50° C. The mixture is completely concentrated by evaporation in vacuo, the residue is dissolved in 200 ml. of methanol and the solution is heated to the reflux temperature for 4 hours. It is then completely concentrated by evaporation in vacuo, the residue is dissolved in 100 ml. of warm ethanol, the solution is cooled to 0° C, and alcoholic hydrochloric acid and 200 ml. of ether are added. After standing at 0° C, the mixture is filtered and the crystals are washed with alcohol/ether and dried.

Yield: 12.0 g. of 2-(2',6'-dichlorophenylamino)-2-imidazoline hydrochloride, representing 90.3% of theory, relative to 2,6-dichloroaniline.

The material is analytically pure.

EXAMPLE 4

16.2 g. of 2,6-dichloroaniline and 22.4 g. of 1-p-toluylimidazolidin-2-one are reacted with 146 ml. of POCl$_3$, and worked up, as described in Example 1.

Yield: 28.3 g. of 1-p-toluyl-(2',6'-dichlorophenylamino)-2-imidazoline, representing 81.3% of theory. The product is purified by recrystallisation from isopropanol.

Melting point 172° to 175° C.

Analysis: C$_{17}$H$_{15}$Cl$_2$N$_3$O: Calculated: C, 58.63; H, 4.34; Cl, 20.36; N, 12.06; O, 4.59. Found: C, 58.8; H, 4.6; Cl, 20.2; N, 11.9; O, 4.9.

pKa: 4.18 (in 70% strength methylCellosolve at room temperature)

UV: $\lambda = 236$ nm (sh, $\epsilon. = 20,200$) in ethanol

IR: (KBr): 3,310 cm$^{-1}$, 1,689 cm$^{-1}$, 1,650 cm$^{-1}$ and 1,620 cm$^{-1}$.

NMR (100 MHz, CDCl$_3$): 3.48 (2H, approximate triplet), 4.07 (2H, approximate triplet), approx. 4.20 (m, broad, NH, exchanges with D$_2$O).

1-p-toluyl-imidazolidin-2-one, used as the starting material is obtained by reaction of ethyleneurea with p-toluyl chloride in the presence of 1-phenyl-2, 3-dimethylpyrazol-5-one at 120° C. Melting point: 198° to 207° C.

EXAMPLE 5

17.5 g. of 1-p-toluyl-(2'-dichlorophenylamino)-2-imidazoline is reacted with 200 ml. of methanol, and worked up, as described in Example 2.

Yield: 13.0 g. of 2-(2',6'-dichlorophenylamino)-2-imidazoline hydrochloride, representing 97.2% of theory; analytically pure.

EXAMPLE 6

2.5 g. of 1-p-toluyl-(2',6'-dichlorophenylamino)-2-imidazoline in 50 ml. of 5% strength acetic acid and 100 ml. of dioxane are boiled for 12 hours under reflux. The mixture is then evaporated to dryness and the residue is digested with water and rendered alkaline with 4 N sodium hydroxide solution. The mixture is extracted three times with ether and the ether phases are combined, washed with water until neutral, dried over sodium sulphate and evaporated. The hydrochloride is prepared from the colorless crystalline residue in the usual manner.

Yield: 1.45 g. of 2-(2',6'-dichlorophenylamino)-2-imidazoline hydrochloride, representing 75.8% of theory; analytically pure.

EXAMPLE 7

3.24 g. of 2,6-dichloroaniline (20 millimols) and 4.5 g. of 1-m-toluylimidazolidin-2-one (22 millimols) in 40 ml of POCl$_3$ are stirred for 70 hours at 50° C. The mixture is then evaporated to dryness in vacuo. The resulting oily residue is taken up in methylene chloride and the resulting suspension is shaken vigorously for about 1 hour with ice and water. The aqueous solution, which reacts strongly acid, is separated off and the organic phase is washed with water. The aqueous extracts are combined and rendered alkaline with saturated sodium carbonate solution, whereupon colorless crystals are obtained. These are filtered off, washed well with water and dried. This gives 5.86 g. of practically pure 1-m-toluyl-2-(2',6'-dichlorophenylamino)-2-imidazoline in a yield of 84.2% of theory, which is recrystallised, for analytical purposes, from isopropanol.

Melting point: 157° to 158° C.

pKa = 4.02 (in 70% strength methylCellosolve at room temperature)

UV: $\lambda = 236$ nm (sh, $\epsilon. = 18,700$) in ethanol

IR: (KBr) 3,430 cm$^{-1}$, 1,680 cm$^{-1}$ and 1,654 cm$^{-1}$

NMR: (100 MHz, CDCl$_3$); 3.48 (2H, approximate triplet), 4.07 (2H, approximate triplet) approx. 4.2 (m, broad, N—H, partially superposed).

1-m-toluyl-imidazolidin-2-one, used as the starting material, was obtained by acylation of N,N'-ethyleneurea with m-toluyl chloride in absolute acetonitrile.

Yield: 86.9%

Melting point: 128° to 129° C.

EXAMPLE 8

4.48 g. of 1-o-toluyl-imidazolidin-2-one is stirred with 3.24 g. of 2,6-dichloroaniline and 30 ml. of POCl$_3$ for 70 hours at 50° C. The excess POCl$_3$ is then removed in vacuo, the residue is suspended in methylene chloride and the suspension is shaken for 1 hour with ice water. The phases are separated, the organic phase is washed with water, the aqueous phases are adjusted to a pH value of 8 to 9 with sodium hydroxide solution and the crystals which precipitate are filtered off, washed and dried. This gives 6.68 g. of crude 1-o-toluyl-2-(2',6'-dichlorophenylamino)-2-imidazoline (96.1% of theory) of melting point: 176° to 177° C. For analysis, this is recrystallised from i-propanol.

Melting point = 179° to 180° C.

pKa: 3.85 (70% strength methylCellosolve, room temperature)

UV: $\lambda = 242$ nm (sh, $\epsilon. = 13,150$) in ethanol

IR: (KBr) 3,355 cm$^{-1}$, 1,706 cm$^{-1}$ and 1,643 cm$^{-1}$.

NMR (100 MHz, CDCl$_3$) 3.94 (2H, approximate triplet), 4.05 and approx. 4.20 (conjointly 3 H, of which 1 H exchangable by D$_2$O, m at 4.05, 2 H remains).

EXAMPLE 9

5.02 g. of 2,6-dibromoaniline and 4.18 g. of 1-benzoylimidazolidin-2-one together with 40 ml. of POCl$_3$ are kept at 50° C for 75 hours, whilst stirring. Excess POCl$_3$ is then thoroughly removed in vacuo and the partially crystalline yellowish-colored residue is digested for about 30 minutes with ice water, with the addition of sufficient saturated sodium carbonate solution to give a pH value of 7 to 8.

The resulting colorless crystals are filtered off, washed well with water and dried. This gives 8.23 g. of crude 1-benzoyl-2-(2',6'-dibromophenylamino)-2-imidazoline (representing 97.6% of theory), which is purified by recrystallisation from isopropanol. 6.30 g. (74.7%) of pure product of melting point 193° to 197° C is obtained.

pKa: 3.67 (in 70% strength methylCellosolve at room temperature)

UV: $\lambda = 240$ nm (sh, $\epsilon. = 17,400$) $\lambda = 290$ nm (sh, $\epsilon. = 3,660$) ethanol IR: (KBr) 3,375 cm$^{-1}$, 1,697 cm$^{-1}$ and 1,638 cm$^{-1}$ NMR: (100 MHz, CDCl$_3$): 3.49 (2H, approximate triplet), 4.11 (2H, approximate triplet), approx. 4.05 (m, broad, N—H, partially masked).

EXAMPLE 10

2.83 g. of 2-chloro-6-methyl-aniline are stirred with 4.18 g. of 1-benzoyl-imidazolidin-2-one and 40 ml. of POCl$_3$ for 70 hours at 50° C. The excess POCl$_3$ is removed in vacuo. Methylene chloride is added to the residue and the mixture is shaken with ice water, 4 N sodium hydroxide solution being added in portions until a pH value of 8 to 9 persists. The phases are then separated and the methylene chloride phase is washed with water, dried and evaporated. 6.09 g. of oily residue is obtained and is triturated with ether and left for some time at room temperature. This gives 3.21 g. (representing 51.4% of theory) of crude 1-benzoyl-2-(2'-chloro-6'-methyl-phenyl-amino)-2-imidazoline. The material is recrystallised from n-hexane, giving an analytically pure product of Melting Point = 124° to 127° C.

UV: 234 nm (sh; $\epsilon. = 16,600$) in ethanol

IR: (KBr) 3,415 cm$^{-1}$ (sharp), 1,673 cm$^{-1}$ and 1,643 cm$^{-1}$

NMR: (100 MHz, CDCl$_3$): 3.37 (2H, approximate triplet) 3.97 (2H, approximate triplet) 4.70 (m, broad, N—H, exchangable with D$_2$O).

EXAMPLE 11

Analogously to the procedure in the preceding Examples, 2,6-dimethylaniline, 1-benzoyl-imidazolidin-2-one and an excess of POCl$_3$ give 1-benzoyl-2-(2',6'-dimethylphenylamino)-2-imidazoline.

Melting point = 124° to 126° C pKa = 6.79 (70% strength methylCellosolve; room temperature)

UV: $\lambda = 228$ nm (sh; $\epsilon. = 16,600$) in ethanol

IR: 3,415 cm$^{-1}$ (sharp), 1,686 cm$^{-1}$, 1,647 cm$^{-1}$ and 1,590 cm$^{-1}$.

NMR: (100 MHz; CDCl$_3$): 4 H of the ethylene group give an approximately centro-symmetrical pattern around 3.74, with the following peaks: 3.49, 3.51, 3.55, 3.57, 3.59, 3.65, 3.68 and 3.79, 3.83, 3.90, 3.92, 3.96 and 3.99.

The N—H exchangable with D$_2$O is at approx. 7.7 and is masked by the aromatic components.

EXAMPLE 12

1.5 g. of 1-benzoyl-2-(2',6'-dichlorphenylamino)-2-imidazoline prepared according to example 1 is boiled under reflux in 25 ml of 5 % sulfuric acid for two hours. After cooling the reaction mixture is brought to alkaline reaction by saturated sodium carbonate solution, whereby an oily substance precipitates, which is extracted with methylene chloride. After washing with water, the solution is dried and evaporated in vacuo. Yield: 1.01 g. 2-(2',6'-dichlorophenylamino)-2-imidazoline, representing 98.2 % of theory as colorless oil, cristallising after standing. Fp.: = 140°– 142° C.

EXAMPLE 13

1.5 g. of 1-benzoyl-2-(2',6'-dichlorophenylamino)-2-imidazoline are reacted with 25 ml of 10 % phosphoric acid and worked up as described in Example 12.

Yield: 0.98 g of 2-(2',6'-dichlorophenylamino)-2-imidazoline, representing 95.3 % of theory. Fp.: 140° – 142° C.

EXAMPLE 14

1.5 g. of 1-benzoyl-2-(2',6'-dichlorophenylamino)-2-imidazoline are reacted with 25 ml of 5 % hydrobromic acid and worked up as described in Example 12.

Yield: 1.0 g. of 2-(2',6'-dichlorophenylamino)-2-imidazoline, representing 97.1 % of theory. Fp.: = 140° – 142° C.

EXAMPLE 15

1.5 g. of 1-benzoyl-2-(2',6'-dichlorophenylamino)-2-imidazoline are reacted with 25 ml of 2 % perchloric acid and worked up as described in Example 12.

Yield: 1.01 g. of 2-(2',6'-dichlorophenylamino)-2-imidazoline, representing 98.2 % of theory. Fp.: = 140° – 142° C.

EXAMPLE 16

1.5 g. 1-benzoyl-3-(2',6'-dichlorophenylamino)-2-imidazoline are reacted with 25 ml of 5 % oxalic acid solution in water and worked up as described in Example 12.

Yield: 1.01 g. of 2-(2',6'-dichlorophenylamino)-2-imidazoline, representing 98.2 % of theory. Fp.: = 140° – 142° C.

EXAMPLE 17

1.5 g. of 1-benzoyl-2-(2', 6'-dichlorophenylamino)-2-imidazoline are reacted with 25 ml of 5 % tartaric acid solution in water and worked up as described in Example 12.

Yield: 1.02 g. of 2-(2', 6'-dichlorophenylamino)-2-imidazoline, representing 99.1 % of theory. Fp.: = 140° – 142° C.

EXAMPLE 18

1.5 g. of 1-benzoyl-2-(2',6'-dichlorophenylamino)-2-imidazoline and 1.25 g of benzoic acid are dissolved in 8 ml of dioxane. 25 ml water are added and the mixture is boiled under reflux for three hours. After reaction is completed the reaction mixture is worked up as in Example 12.

Yield: 0.99 g. of 2-(2',6'-dichlorophenylamino)-2-imidazoline, representing 96.2 % of theory. Fp.: = 140° – 142° C.

EXAMPLE 19

1.5 g. of 1-benzoyl-2-(2',6'-dichlorophenylamino-2-imidazoline and 25 ml of propionic acid are dissolved in 10 ml of dioxane and are boiled under reflux for three hours. The reaction mixture is worked up as Example 12.

Yield: 0.97 g. of 2-(2',6'-dichlorophenylamino)-2-imidazoline, representing 94.1 % of theory. Fp.: = 140° – 142° C.

EXAMPLE 20

1.5 g. of 1-benzoyl-2-(2',6'-dichlorophenylamino)-2-imidazoline and 25 ml ethanolamine are heated to 100° C whilst stirring for three hours. The resulting green-brown colored solution is evaporated to dryness in vacuo and the residue is triturated with 20 ml of water, whereby crystallization occurs. The precipitate is filtered off, washed with water and dried.

Yield: 0.95 g. of 2-(2',6'-dichlorophenylamino)-2-imidazoline, representing 92.2 % of theory. Fp.: = 140° – 142° C.

EXAMPLE 21

1.5 g. of 1-benzoyl-2-(2',6'-dichlorophenylamino)-2-imidazoline are dissolved in 20 ml of acetonitrile, 16 ml of water, and 4 ml of saturated solution of potassium carbonate are added and refluxed for 3,5 hours. After removing the organic solvent in vacuo as completely as possible, the aqueous solution is extracted (twice) with 25 ml-portions of $CH_2Cl_2$, the combined organic phases are washed with water, dried and evaporated. The residual colorless resin cristallises.

Yield: 1.00 g. of 2-(2',6'-dichlorophenylamino)-2-imidazoline, representing 97.1 % of theory. Fp.: = 140° – 142° C.

What we claim is:

1. A process for the preparation of a 2-arylamino-2-imidazoline derivative selected from the group consisting of a compound having one of the formulas

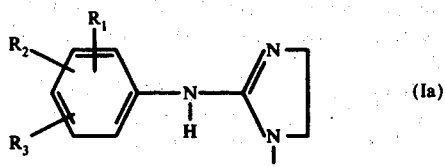 (Ia)

or

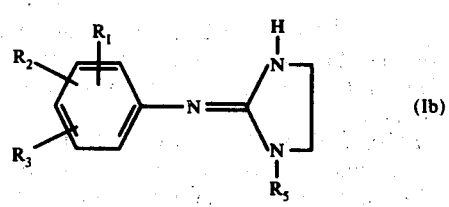 (Ib)

in which each of $R_1$, $R_2$ and $R_3$, which may be the same or different, are selected from the group consisting of hydrogen, halogen, lower alkyl, lower alkoxy and the nitro group, with the proviso that in every case at least one of $R_1$, $R_2$ and $R_3$ is not hydrogen and $R_5$ is selected from the group consisting of benzoyl, methylbenzoyl- and ethylbenzoyl and an acid addition salt thereof which comprises reacting an aniline derivative of the formula

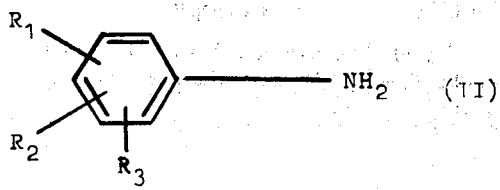 (II)

in which $R_1$, $R_2$ and $R_3$ are defined as above, with an 1-aroyl-imidazolidin-2-one having the formula

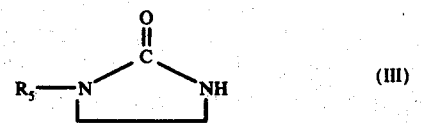 (III)

in which $R_5$ is as defined above, in the presence of at least 2 mols of phosphorus oxychloride per mol of the aniline derivative of the formula II, at a temperature from room temperature to the boiling point of phosphorus oxychloride and subjecting the intermediate compound after removing excess phosphorus oxychloride to mild hydrolysis, after which, the compounds of formula Ia or Ib respectively are isolated as free base or as a salt by adding an inorganic or organic acid.

2. A process as claimed in claim 1, in which more than 3 mols of phosphorus oxychloride are employed per mol of aniline derivative of the formula II.

3. A process as claimed in claim 1, in which the reaction is carried out in excess phosphorus oxychloride as the solvent.

4. A process for the preparation of a 2-arylamino-2-imidazoline derivative selected from the group consisting of a compound of one of the formulas

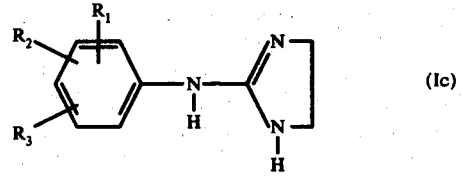 (Ic)

or

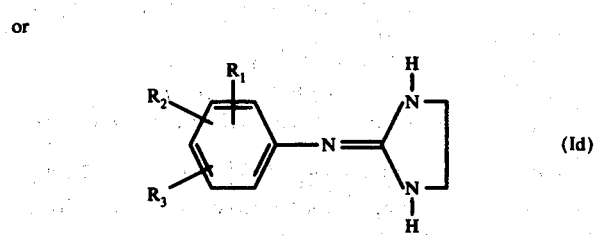 (Id)

in which each of $R_1$, $R_2$ and $R_3$, which may be the same or different, are selected from the group consisting of hydrogen, halogen, lower alkyl, lower alkoxy and the nitro group, with the proviso that in every case at least one of $R_1$, $R_2$ and $R_3$ is not hydrogen and an acid addition salt thereof, which comprises reacting an aniline derivate of the formula

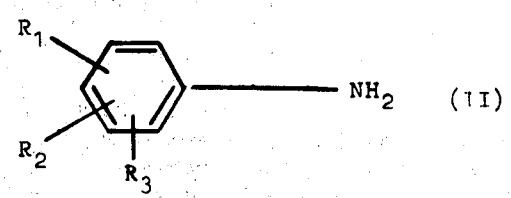 (II)

in which $R_1$, $R_2$ and $R_3$ are defind as above, with an 1-aroylimidazolin-2-one having the formula

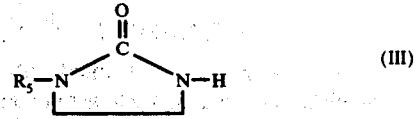 (III)

in which $R_5$ is selected from the group consisting of benzoyl, methylbenzoyl and ethylbenzoyl in the presence of at least 2 mols of phosphorus oxychloride per mol of the aniline derivative of the formula II, at a temperature from room temperature to the boiling point of phosphorus oxychloride and subjecting the intermediate compound obtained after removing excess phosphorus oxychloride to mild hydrolysis, after which in the resulting compound of the formulas

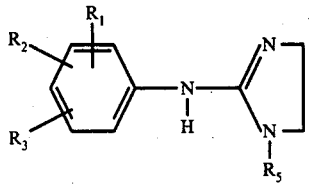

(Ia)

or

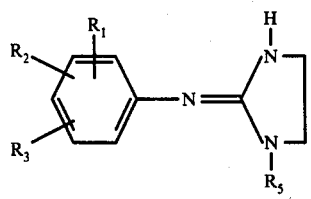

(Ib)

in which $R_5$ is as defined above, the group $R_5$ is split off by treatment with a splitting agent selected from the group consisting of lower aliphatic monoalcohols, mineral acids, monocarboxylic acids, polycarboxylic acids, sodium hydroxide solution, potassium hydroxide solution, salts of sodium or potassium, the aqueous solutions of which give an alkaline reaction, ammonia, amines, cyclic imines and akali alcoholates for more than one hour and the compounds of formula Ic or Id respectively are isolated as free base or as a salt by adding an inorganic or organic acid.

5. A process as claimed in claim 4, in which more than 3 mols of phosphorus oxychloride are employed per mol of aniline derivative of the formula II.

6. A process as claimed in claim 4, in which the reaction is carried out in excess phosphorus oxychloride as the solvent.

7. A process as claimed in claim 4, in which the splitting agent is a lower aliphatic primary alcohol and the reaction is carried out at elevated temperature.

8. A process according to claim 4, in which 2-(2',6'-dichlorophenylamino)-2-imidazoline is prepared by reacting 2,6-dichloroaniline with an 1-aroylimidazolidin-2-one of formula III above in the presence of at least 2 mols of phosphorus oxychloride per mol of 2,6-dichloraniline and freeing the reaction mixture from excess phosphorus oxychloride by evaporation and immediately reacting the resulting mixture with the splitting agent.

9. The compound selected from the group consisting of a compound having one of the formulas

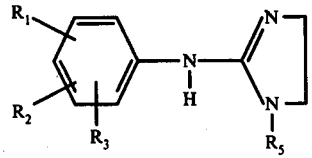

(Ia)

or

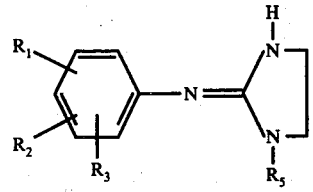

(Ib)

in which each of $R_1$, $R_2$ and $R_3$, which may be the same or different, are selected from the group consisting of hydrogen, halogen, lower alkyl, lower alkoxy and the nitro group, with the proviso that in every case at least one of $R_1$, $R_2$ and $R_3$ is not hydrogen and $R_5$ is selected from the group consisting of benzoyl, methylbenzoyl and ethylbenzoyl and an acid addition salt thereof.

10. As a compound as claimed in claim 9, 1-Benzoyl-2-(2',6'-dichlorophenylamino)-2-imidazoline of melting point 160° to 162° C and pKa value 4.01.

11. As a compound as claimed in claim 9, 1-Benzoyl-2-(2',6'-dibromophenylamino)-2-imidazoline of melting point 193° to 197° C and pKa value 3.67.

12. As a compound as claimed in claim 9, 1-p-Toluyl-(2',6'-dichlorophenylamino)-2-imidazoline of melting point 172° to 175° C and pKa value 4.18.

13. As a compound as claimed in claim 9, 1-o-Toluyl-(2',6'-dichlorophenylamino)-2-imidazoline of melting point 179° to 180° C and pKa value 3.85.

14. As a compound as claimed in claim 9, 1-m-Toluyl-(2',6'-dichlorophenylamino)-2-imidazoline of melting point 157° to 158° C and pKa value 4.02.

* * * * *